United States Patent [19]

Scarberry

[11] 4,351,330

[45] Sep. 28, 1982

[54] EMERGENCY INTERNAL DEFIBRILLATION

[76] Inventor: Eugene N. Scarberry, 2834 Durban, Houston, Tex. 77043

[21] Appl. No.: 186,412

[22] Filed: Sep. 12, 1980

Related U.S. Application Data

[63] Continuation-in-part of Ser. No. 873,517, Jan. 30, 1978, Pat. No. 4,231,365.

[51] Int. Cl.³ .......................................... A61M 25/00
[52] U.S. Cl. ........................... 128/207.15; 128/419 D; 128/786; 128/787; 128/784
[58] Field of Search .............. 128/207.15, 419 D, 787, 128/786, 784, 419 P

[56] References Cited

U.S. PATENT DOCUMENTS

| | | | |
|---|---|---|---|
| 3,683,908 | 8/1972 | Michael et al. | 128/145.7 |
| 3,874,377 | 4/1975 | Davidson | 128/145.5 |
| 4,088,138 | 5/1978 | Diack et al. | 128/419 D |
| 4,090,518 | 5/1978 | Elam | 128/349 B |
| 4,231,365 | 11/1980 | Scarberry | 128/207.15 |

OTHER PUBLICATIONS

Advances in Cardiopulmonary Resuscitation, 1977, by Elam et al., pp. 65-72.

*Primary Examiner*—Henry J. Recla
*Attorney, Agent, or Firm*—Carwell & Helmreich

[57] ABSTRACT

An emergency resuscitation and defibrillation apparatus is provided by an endotracheal tube having a tracheal obturator and a second expandable cuff for sealing against the pharyngeal tissues to provide an alternate sealing means for respiratory fluids if the blind intubation is not successful. A laryngeal tube passes through this pharyngeal obturator for alternatively introducing respiratory fluids into the lungs through the larynx. The endotracheal tube may also be used as an esophageal obturator and inserted without the intubating guide means. Two internal electrode areas are provided; one of which may be in the oral region for contacting the tongue and one of which may be in the esophagus for contacting the esophageal wall. An internal conducting path is formed thereby for introducing electrical stimuli suitable for terminating cardiac fibrillation and other arrythmias. The endotracheal and laryngeal tubes may be individually accessed from outside the patient to ensure proper placement of the internal electrodes.

17 Claims, 4 Drawing Figures

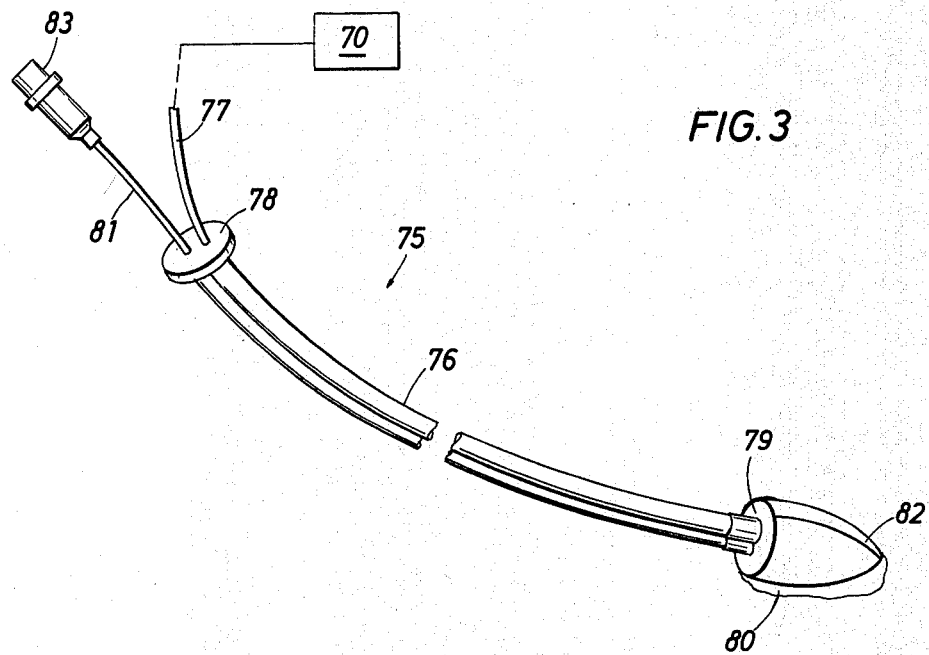
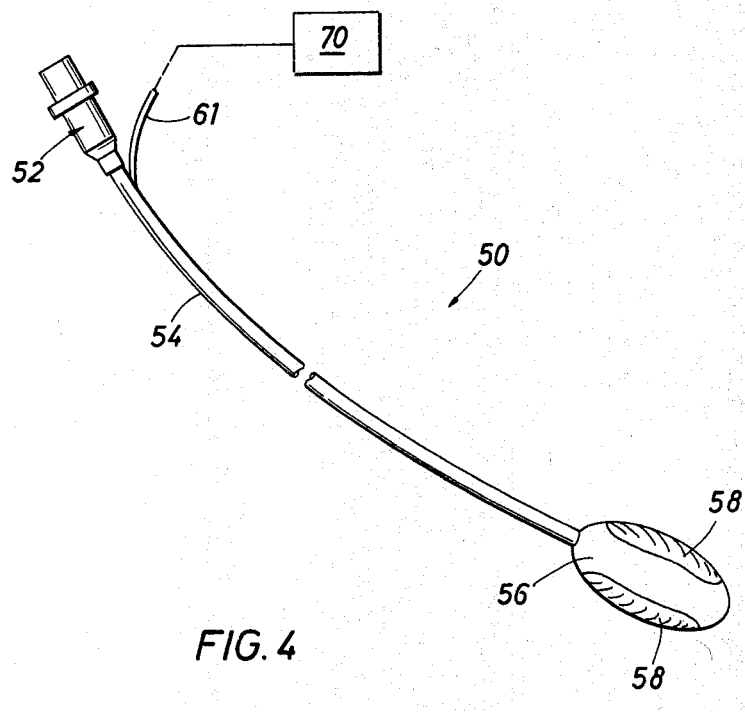

EMERGENCY INTERNAL DEFIBRILLATION

RELATED CASES

This application is a continuation-in-part of U.S. patent application Ser. No. 873,517, filed Jan. 30, 1978 now U.S. Pat. No. 4,231,365.

FIELD OF THE INVENTION

This invention relates to emergency medical apparatus and, more particularly, to emergency apparatus for artificial respiration and cardiac defibrillation.

BACKGROUND OF THE INVENTION

Artificial respiration or resuscitation techniques now being used to revive a victim without normal respiratory function involve the introduction of a fluid, such as oxygen or air, directly into the patient. In the most rudimentary form, this is accomplished by "mouth-to-mouth" respiration where a medical attendant or the like exhales directly into the mouth of the patient, thereby forcing air into the lungs.

A more satisfactory technique involves intubation, where a hollow tube is inserted through the mouth and into the proximity of the larynx. Yet another improvement involves sealing off the esophagus in order to prevent diversion of respiration effort to inflation of the stomach. In addition, an open esophagus can result in aspiration of the stomach contents through the esophagus into the mouth and throat, and subsequently into the respiratory passages. The occurrence of such backflow could result in the inability of the lungs to receive the fluid needed for respiration.

One prior art device is an endotracheal tube which is inserted through the mouth of the patient, through the laryngeal region and into the patient's trachea. Yet another prior art device, depicted in U.S. Pat. No. 3,683,908, embodies an esophageal obturator where an elongated tube carries an expandable device into the patient's esophagus, the expandable member to obturate, or block off, the esophagus. Still another prior art device is described in an article by Elam et al., *Advances in Cardiopulmonary Resuscitation*, 1977, pages 65–72, wherein an esophageal obturator is combined with a pharyngeal cuff to obviate the need for a sealing face mask. U.S. Pat. No. 3,874,377 to Davidson discloses an insertable tube including a rotating valve-like member for use in sealing either the esophagus or the trachea.

In dealing with emergency conditions requiring artificial resuscitation, it is not uncommon to encounter associated cardiac arrythmias. Prior art devices have included a single internal electrode coupled with an external electrode to provide electrical stimulation to the heart suitable for arresting the arrythmia and/or restoring normal operation of the heart.

As noted in U.S. Pat. No. 4,090,518 to Elam, such a device requires energy levels of 15 to 20 watt seconds. Although these current levels are an improvement over the energy levels of about 400 watt seconds required by two external electrodes, the levels are significantly above the energy levels of 1–10 watt seconds where direct heart contact is made. It would be desirable to obtain defibrillation using smaller current levels to improve the portability of power supplies for defibrillation units but without the need for surgery to obtain direct heart contact.

The disadvantages of the prior art are overcome by the present invention, however, and improved apparatus for emergency artificial respiration and cardiac defibrillation are provided.

SUMMARY OF THE INVENTION

In a preferred embodiment of the present invention, an endotracheal tube having a stylet bullet guide performed to enter the region adjacent the trachea and having an obturator is provided for blind intubation of the trachea where emergency resuscitation is required. A pharyngeal obturator is provided for sealing the upper portion of a patient's airway to prevent the flow of fluids back through the pharynx and out the mouth and nose passages if the blind endotracheal intubation does not succeed. An electrode area may be provided on the pharyngeal obturator for contacting a portion of the tongue as an upper electrode.

A duct is provided through the pharyngeal cuff for introducing respiratory fluids into the laryngeal region of the patient when the pharyngeal cuff is inflated. If desired, the endotracheal tube may be inserted without the bullet guide and serve as an esophageal obturator to seal the interior of the esophagus so that respiration fluid is confined exclusively to the lungs and to provide an electrode surface adjacent the esophageal wall at a location in proximity to the heart. The stylet or a separate catheter may also be used to position an electrode in the esophagus at a location proximate to the heart to obtain the selected internal electrode configuration. Depending on the location of the endotracheal tube, either the endotracheal tube or the laryngeal tube could be used to insert the stylet or catheter.

A face shield may be provided to support and position the various tubes inserted into the patient and to facilitate insertion to the proper location. The face shield is not required to seal about the facial contours but is sized to preclude ingestion through the mouth. The shield may also incorporate an electrode area for contacting the tongue.

The endotracheal tube may be inserted alternatively into the esophagus to communicate with the stomach to provide for the introduction of fluids into the stomach or the release of gases and/or fluids from the stomach, if desired, or to provide an electrode area contacting the esophageal walls. Such a device may conveniently have a cap or a pressure-indicator balloon over the outer end which would indicate the presence of fluid inside the tube from the stomach region.

The laryngeal and pharyngeal obturators are preferably inflatable members which may be inflated by merely blowing into the members through a suitable mouthpiece. The mouthpiece may be provided with a pressure relief valve to prevent over-pressurizing the obturators and damaging the surrounding tissue. Further, supply lines leading to the inflatable obturators may be equipped with check valves for maintaining fluid inside the obturators until the check valves are open to release the fluid.

It is a primary feature of the present invention to provide internal electrodes in an emergency resuscitation apparatus contacting the patient at locations effective to form a defibrillating current path.

It is another feature of the present invention to combine an endotracheal tube and pharyngeal obturator to insure that respiratory fluid is confined to the lungs and yet provide for proper placement of the internal electrodes.

It is yet another feature of the present invention to provide an emergency resuscitation and cardiac defibrillation device which can be utilized by emergency medical personnel at locations remote from a hospital.

Yet another feature of the present invention is to provide an emergency medical resuscitation and cardiac defibrillation apparatus which can be operated by only one person if manual respiration is required.

Still another feature of the present invention is to employ inflatable members as obturators and as electrode areas which may be inflated by the human breath to sealingly engage and urge the electrodes against surrounding tissue without damage to that tissue.

These and other features and advantages of the present invention will become apparent from the following detailed description, wherein reference is made to the figures in the accompanying drawings.

IN THE DRAWINGS

FIG. 3 is a pictorial view of a preformed stylet.

FIG. 4 is a pictorial view of a catheter-carried electrode.

DETAILED DESCRIPTION OF THE DRAWINGS

Figure 1:
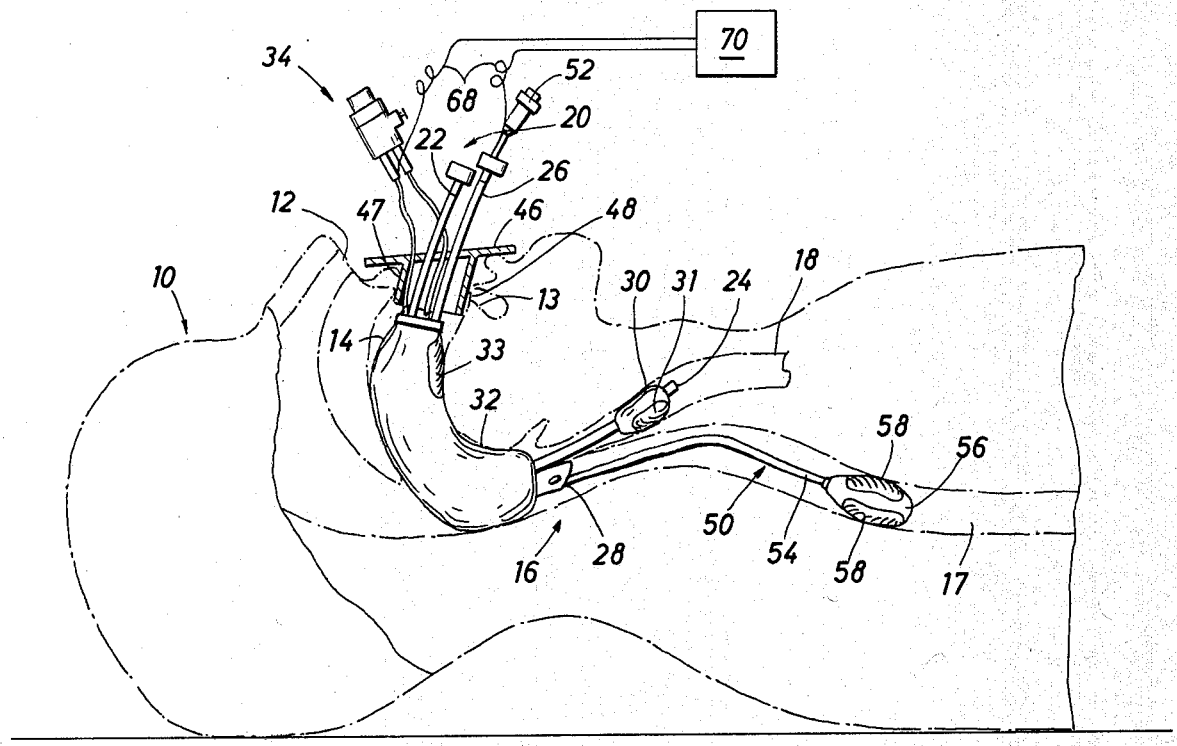
FIG. 1 is a pictorial illustration, partly in cross section, showing one embodiment of the present invention properly inserted into a patient.

Referring now to FIG. 1, there may be seen a pictorial view, partly in cross section, of an endotracheal airway 20 properly inserted in patient 10. A pharyngeal cuff 32 has been inserted into the pharynx at a location which effectively blocks both nasal passage 12 and oral passage 14 and, if inflated, prevents the flow of fluids from these passages into or out of patient 10. A laryngeal tube 26 is provided with an opening adjacent inner end 28 for the purpose of introducing a respiratory fluid into the trachea 18 of patient 10, if needed, or to insert an electrode-carrying catheter into the esophagus. Laryngeal tube 26 passes through the inflated pharyngeal cuff 32. Endotracheal tube 22 is provided for the primary purpose of introducing respiratory fluid into the patient's trachea through inner end opening 24.

Tracheal cuff 30 and pharyngeal cuff 32 may conveniently be expanded by introducing an inflating fluid through cuff inflator means 34 which is interconnected with inflatable cuffs 30 and 32. Electrode areas 31 and 33 may be included on cuffs 30 and 32 for providing internal electrical contacts for applying a defibrillating current to the patient.

Face shield 46 may be placed over a portion of the face of patient 10 and serves to properly position laryngeal tube 26 and endotracheal tube 22 within patient 10. Further, shield 46 insures that none of the apparatus is ingested by patient 10. A teeth shield 47 may be provided to preclude damage to the tubular members from voluntary or involuntary reflex movement by the mouth. An electrode area 48 may be included for forming a first internal electrode contact, preferably on the tongue.

In FIG. 1, endotracheal tube 22 is properly in the trachea and inner end 24 serves to introduce respiratory fluid into the lungs. Tracheal cuff 30 seals the trachea against escape of the respiratory fluid. Proper insertion may be accomplished by inserting a relatively stiff stylet bullet guide (see FIG. 3) into tube 22 where the stylet is preshaped to enhance blind entry of inner end 24 into the trachea. If inner end 24 misses the trachea, it will enter the esophagus 17 and be available as an esophageal obturator and either an upper or lower internal electrode, as hereinafter discussed.

It may be seen from FIG. 1 that pharyngeal cuff 32 is inserted adjacent a portion of the pharynx 16 and to a position to effectively block both oral passage 14 and nasal passage 12. The pharynx comprises the soft, muscular and membranous cavity portion of the alimentary canal leading from the mouth and nasal passages to the larynx and esophagus. It is desired that pharyngeal cuff 32 seal both the oral and nasal regions of pharynx 16 and that electrode area 33 forms an electrical contact with adjacent body tissue. Accordingly, it is desirable to utilize a relatively low pressure to inflate pharyngeal cuff 32 in order to prevent damage to these soft tissues.

When properly inserted, emergency endotracheal airway 20 serves to seal the interior of trachea 18 by inflating tracheal obturator 30 to engage the interior of trachea 18 and/or to seal the pharynx 16, if needed, by inflating pharyngeal obturator 32. The respiratory fluid is introduced into endotracheal tube 22 and exits directly in the trachea. If endotracheal tube 22 misses the trachea, and enters esophagus 17, then both obturators 30 and 32 may be inflated to seal the trachea. The respiratory fluid is then confined to the portion of the body leading to the lungs and enters generally into larynx 18, and thence, into the trachea and lungs. No resuscitation fluid is expended inflating the stomach and the stomach contents cannot aspirate into the lungs.

As depicted in FIG. 1, electrodes are included on the emergency resuscitation apparatus for contacting internal body tissue to provide an electrical current suitable for terminating a cardiac arrythmia such as fibrillation. Where internal electrical contact is made, skin resistance is avoided and lower current inputs may be used to obtain the desired current adjacent the heart. It is expected that energy input levels of about 10 watt seconds will be sufficient, compared with energy levels of about 400 watt seconds where only external contact electrodes are used.

A first preferred internal electrode contact area is the tongue 13. Teeth shield 47 may conveniently include an electrically conductive area 48 for contacting tongue 13. Since teeth shield 47 is generally rigid, the electrode may be easily affixed thereto, for example by plating on the surface or by adhesively affixing an electrode depending therefrom. An alternative or an additional electrode area 33 may be provided on laryngeal obturator 32 adjacent the tongue. U.S. Pat. No. 4,090,518 to Elam teaches suitable techniques for providing an electrode area on an inflatable cuff using a folded cuff or constructing the cuff of a conductive material, which disclosure is incorporated herein by reference. Alternatively, the electrode area may be formed in an expandable pattern on the obturator or plated onto an inflatable, but non-expandable, cuff.

One or more electrical leads 68 are connected with electrode areas 48 and/or 33 and brought to an external location in any convenient manner. A conventional portable defibrillator power supply 70 may be connected using power settings generally associated with heart stimulation using direct contact electrodes.

The lower, second electrode contact area is adjacent the location of the heart to provide current flow through the heart. The esophagus 17 may conveniently be used for inserting an electrode to a proper location.

As depicted in FIG. 1, tracheal obturator 30 has been inserted in the trachea 18, a preferred location for ventilating a patient. It will be noted, however, that the tracheal location is not considered optimum for locating the lower electrode since the heart would be below the electrode area.

Electrode 31 may nevertheless by included on tracheal obturator 30 to increase the flexibility for using the inserted device. If the tracheal obturator 30 does enter the esophagus, it may be inserted to a position effective to defibrillate the heart without the need to insert an internal electrode catheter 50 (FIG. 4), as hereinafter described. It may also be possible to establish an internal defibrillating path from electrode 31 in the trachea to an internal electrode catheter 50 in esophagus 17.

Where tracheal obturator 30 is within trachea 17, it is preferable to provide electrode catheter 50 (FIG. 4) to establish electrical contact within esophagus 17 at a location adjacent the heart. Electrode catheter 50 may conveniently be inserted through laryngeal tube 26, which is not required for resuscitation purposes. Inflation piece 52 is included for expanding electrode cuff 56 urging electrode areas 58 against the wall tissue of esophagus 17. Thus, the required internal current path is established between electrode areas 58 and at least one of electrodes 48, 33 or 31 to defibrillate a patient while maintaining artificial respiration.

It will be appreciated that the emergency apparatus depicted in FIG. 1 is entirely suitable for use by a single trained technician. Pharyngeal cuff 32 permits the apparatus to be operated without a sealing face mask. The operator is thus free to activate the defibrillating unit 70. Since all of the electrical contact areas are internal to the patient, the technician has free hands to maintain emergency resuscitation while simultaneously engaging and operating the defibrillating system.

Figure 2:
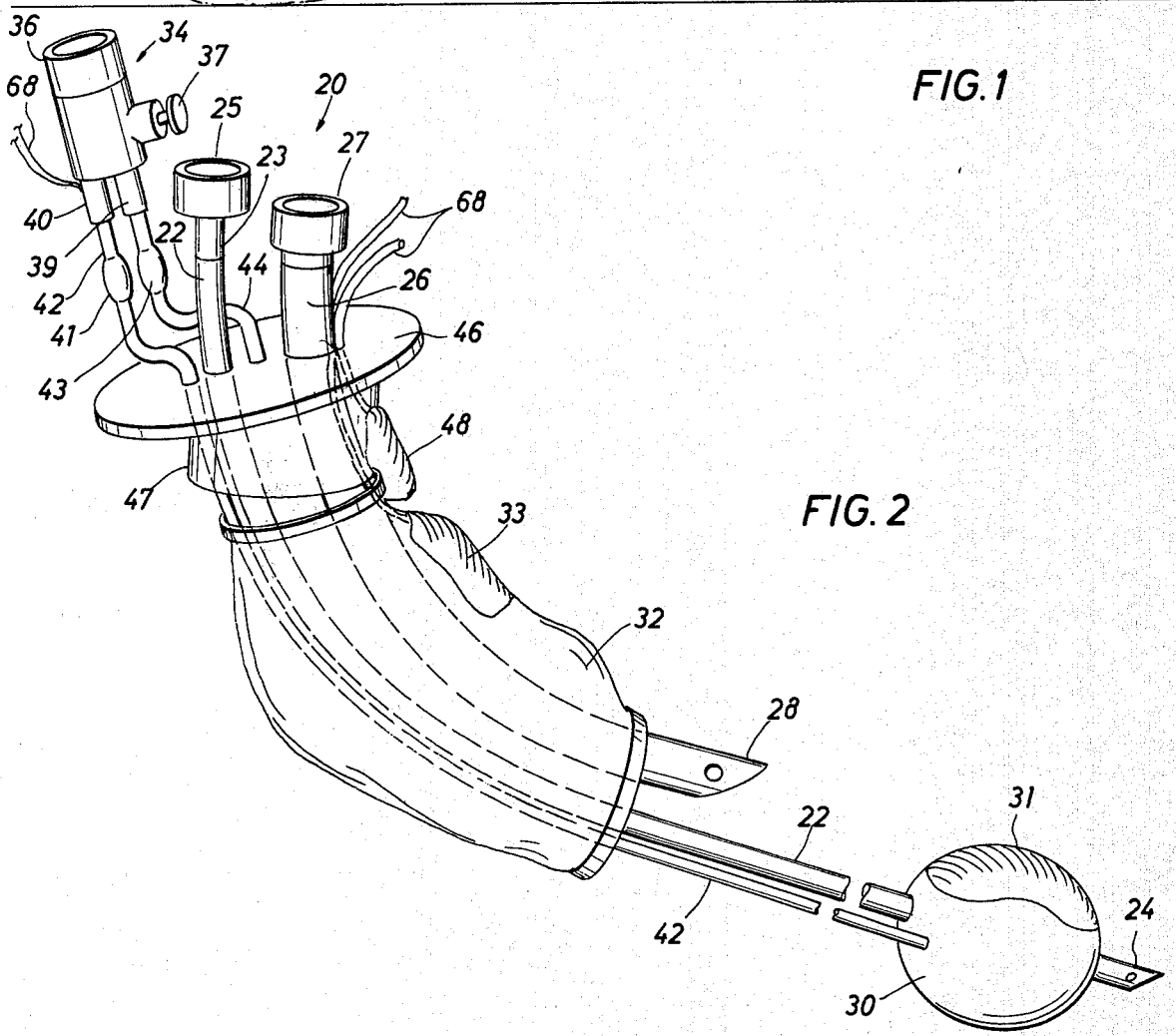
FIG. 2 is a pictorial view of one embodiment of the emergency apparatus.

Referring now to FIG. 2, there may be seen a pictorial illustration of a preferred embodiment of the present invention. Emergency endoracheal airway 20 includes an expandable tracheal cuff 30 carried by endotracheal tube 22 and an expandable pharyngeal cuff 22. Laryngeal tube 26 is provided with an outer end 27 and an inner end 28 whereby resuscitation fluid which is introduced into outer end 27 exists through inner end 28. Laryngeal tube 26 passes through pharyngeal cuff 32 and may be sealed about the entrance and exit or may be sealed exteriorly of cuff 32 as cuff 32 expands to surround tube 26. The length of laryngeal tube 26 is preferably about 90-100 mm to obtain a penetration into a patient to a region adjacent the larynx without activating the epiglottis and closing the larynx. A standard tube diameter of 10 mm may be conveniently selected for this tube.

Pharyngeal cuff 32 is formed along laryngeal tube 26 and endotracheal tube 22 and may be sealed about tubes 26 and 22 or may simply seal around tubes 26 and 22 when expanded. Pharyngeal cuff 32 is designed to obturate, or block, the pharyngeal region beneath the oral and nasal openings. Pharyngeal cuff 32 generally takes the form of an expandable element which is generally expanded by inflating with the pressurized fluid. It is desirable that pharyngeal cuff 32 be inflatable at a relatively low pressure, e.g. about 0.5 psi, in order to prevent damage to the surrounding pharyngeal tissue. An electrode area 33 may be conveniently located adjacent the upper portion of cuff 32 to obtain electrical contact with the patient's tongue. It is desirable to maintain the area of electrode 33 as large as conveniently possible to minimize the current density and damage to surrounding tissue. Electrode area 32 is connected to one of the electrical leads 68. If a low pressure inflation is used, the surface area of cuff 32 must be sufficient to exert enough total force on the surrounding pharyngeal tissue to limit or prevent the escape of fluids between pharyngeal cuff 32 and the surrounding tissues.

It should be noted that pharyngeal cuff 32 may be bifurcated where a first, low pressure cuff is inflated adjacent the soft oral tissues. A second, higher pressure cuff might then be provided for use in the portion of the pharynx adjacent the larynx. This bifurcated obturator would ensure that proper sealing results.

Referring again to FIG. 2, there is also seen endotracheal tube 22 having tracheal obturator 30 adjacent inner end 24. In one embodiment, endotracheal tube 22 is hollow and inner end 24 defines an opening to the lungs, or to the stomach if used as an esophageal obturator. Thus, the lungs or the stomach region can be accessed through tube 22. Endotracheal tube 22 may also be provided with an indicator device 25 at outer end 23 for indicating the presence of a fluid within tube 22. Such an indicator means may simply take the form of a flexible member which inflates when pressurized by gases and/or other fluids entering endotracheal tube 22 from the lungs or the stomach. If an indicator device is not required, outer end 23 may simply be capped or may even remain open. The total length of endotracheal tube 22 may conveniently be 200-230 mm in order to place inner end 24 positively within the trachea.

The endotracheal tube may be provided with electrode regions 31, which may be connected to external electrical lead 68 possibly carried within inflation tube 43. In this case, a longer tube 22 may be provided to permit insertion into the esophagus a distance effective to defibrillate the heart. Tube 22 may then have two markings, or stops (not shown), to indicate the desired depth of insertion.

FIG. 3 depicts a stylet bullet guide 75 for inserting inner end 24 of tube 22 into the trachea. Guide 75 has a cap 78 which rests against the top surface of filling 25 and may serve to seal the interior of tube 22. A stylet or guide portion 76 is formed from a suitable thermoplastic to assume a shape cooperating with the pharynx and larynx to place inner end 24 in the trachea. Bullet 79 protrudes from inner end 24 for non-traumatic insertion of inner end 24. Bullet 79 may be fabricated from a soft, pliant material to minimize any trauma to the vocal cords during traverse of bullet 79. After insertion, bullet 79 and guide 76 are sized to be withdrawn through endotracheal tube 22 and allow access to the lungs. For esophageal use, stylet guide 75 may remain in place as a seal. A properly shaped stylet 76 generally increases the success rate for blind intubation from 10-20% to about 50%.

Stylet 75 may also be designed to provide an electrode surface 82 for contacting the esophageal walls. Inflatable cuff 80 may be inflated through tube 81 using fluid inlet means 82 to urge electrode 82 into engagement with surrounding tissue. Electrical lead 77 may be conveniently connected to electrode 82 and molded within stylet body portion to provide external connection with defibrillator power supply 70. A first removable stop (not shown) may be provided for use in inserting tracheal tube 22. If esophageal intubation is obtained rather than tracheal intubation, the stylet may be further inserted to the desired location and cuff 80 inflated to urge electrode 82 into electrical contact with the esophagus. If tracheal intubation is obtained, stylet 75 may then be removed from endotracheal tube 22 and reinserted through laryngeal tube 26 (see FIG. 2) to the desired electrode 82 location.

Tracheal obturator 30 may be expanded in several ways, both by mechanical mechanisms and by inflation. A variety of obturators are shown in U.S. Pat. No. 3,683,908, and any one of them may be used in conjunction with the present invention. If, however, a low pressure device is chosen for pharyngeal obturator 32, it would be desirable to also provide a low pressure device for tracheal obturator 30 in order that both will inflate and seal at the same pressure. Accordingly, a suitable tracheal obturator would provide sufficient surface area in contact with the interior walls of the trachea or esophagus to exert sufficient force to limit or prevent the passage of fluid between an inflated tracheal obturator 30 and the interior of the trachea or esophagus.

A cuff inflator means 34 is also shown in FIG. 2. Cuff inflator means 34 includes a fluid inlet 36 to which the inflating fluid is introduced. The inflating fluid may pass through check valves 39 and 40 and into tubes 44 and 42, respectively, for inflating pharyngeal cuff 32 and tracheal cuff 30, respectively. Tubes 42 and 44 may conveniently be equipped with pressure indicator balloons 41 and 43 which expand to a diameter somewhat greater than the diameter of tubes 42 and 44. A visual observation is thus provided of the presence or absence of pressurizing fluid within expandable cuffs 32 and 30. A pressure relief valve 37 may be included on fluid inlet 36 in order to prevent overpressurizing expandable cuffs 32 and 30 and subsequent tissue damage.

Alternately, cuff inflator means 34 may simply consist of a fluid inlet 36 interconnected with tubes 42 and 44. Pressure relief valve 37 may be omitted where human breath is being used to inflate cuffs 30 and 32. It has been determined that a maximum pressure of only about 120 cm of H₂O can be obtained where human breath is used, and this pressure will not generally traumatize the tissues surrounding cuffs 30 and 32. If further simplification of cuff inflator means 34 is desired, check valves 39 and 40 may be removed and any convenient external clamp may be employed to prevent the release of pressure from cuffs 30 and 32.

Various alternate means may be provided to inflate cuffs 32 and 30. Individual fluid inlets 36 might be required if expandable cuffs 32 and 30 are designed to require different pressures for proper inflation and sealing. Alternatively, if a single inflation pressure is chosen, it is possible to combine inflation tubes 42 and 44 into a single tube which inflates both pharyngeal cuff 32 and tracheal cuff 30.

Yet another cuff for use as pharyngeal obturator 32 or tracheal obturator 22 embodies a normally expanded material which sealingly engages the pharynx and trachea. The normally expanded material would retract upon the application of a vacuum device for insertion or removal. Once inserted, however, the cuffs remain expanded in the event of any system failures and the emergency resuscitation can continue.

In a preferred embodiment of the present invention, outer end 27 of laryngeal tube 26, outer end 23 of endotracheal tube 22, and fluid inlet 36 are provided with standard 15 mm fittings for interconnecting with commercially-available respiration and inhalation equipment. A suitable tracheal obturator may be spherical or cylindrical, having a diameter of 4–5 mm and a length of about 4 cm. The inflatable cuffs are preferably of a thin, flexible material which does not damage surrounding tissue. Pharyngeal tube 26 and endotracheal tube 22 are preferably formed of a thermoplastic-type material which is flexible but which will retain a permanent set when formed at a selected temperature and thereafter cooled. Thus, these tubes may be curved in a conventional manner to facilitate entry through the oral cavity, with the elongated tracheal tube 22 formed to guide itself into the trachea in cooperation with stylet bullet guide 75.

Referring again to FIG. 2, there is seen face shield 46. Shield 46 is designed to fit over a portion of the face, and more particularly the oral cavity. Shield 46 is sufficiently large that it cannot be accidently ingested by a patient. Electrode 48 may be incorporated on teeth shield 47 at a location effective to engage the tongue. Electrode 48 may be formed to depend from shield 47 to enhance electrical contact with the tongue. Electrical leads 68 are provided to connect electrode 48 with a suitable power supply. Pharyngeal tube 26 and endotracheal tube 22 may be force-fit into face shield 46 to predetermined lengths so that tubes 22 and 26 will be in the correct location when emergency endotracheal airway 20 has been inserted and shield 46 rests adjacent the face of the patient.

If desired, the outer end 23 of endotracheal tube 22 may be force-fit into shield 46 so that shield 46 may be removed from about outer end 23 or endotracheal tube may be further inserted to position electrode 31. Then, when endotracheal tube 22 is inserted into the patient's trachea, shield 46, tracheal tube 26 and pharyngeal cuff 32 may be removed from about endotracheal tube 22 and cuff 30 may be inflated to seal about the interior of the trachea and the respiratory fluid introduced directly through esophageal tube 22. It is anticipated that pharyngeal cuff 32 and laryngeal tube 26 will normally remain in place to back up endotracheal tube 22.

Alternative embodiments of the resuscitation apparatus described in FIG. 2 are described in co-pending U.S. patent application Ser. No. 873,517, which disclosure is incorporated herein by reference. Each of the disclosed embodiments is suitable to obtain the electrode areas and defibrillating current paths hereinabove explained for purposes of the present invention.

Referring now to FIG. 4, there is shown an electrode catheter 50 for use in obtaining the lower electrode contact in the esophagus rather than attempting to incorporate electrodes on the endotracheal obturator 30 (FIG. 2) or the stylet 75 (FIG. 3). Catheter 50 consists of an inflatable cuff 56 having electrode areas 58 in accordance with one of the designs hereinabove discussed. Tube 54 may be used to inflate cuff 56 and to house electrical lead 61 connecting electrodes 58 with power supply 70. Inflation fluid is introduced through fluid inlet 52. Tube 54 has a diameter to permit insertion through either endotracheal tube 22 or laryngeal tube 26 (see FIG. 2) and a length effective to position electrode leads 58 adjacent the heart.

In the event of an emergency requiring artificial resuscitation, a medical technician or lay person trained in emergency first-aid should be able to use the apparatus which is the subject of the present invention without undue difficulty. A method using the device depicted in FIG. 2 will be described, although the operation is substantially identical for all embodiments of the invention.

In a preferred embodiment, the endotracheal and laryngeal tubes, along with the associated obturators, are pre-coated with a suitable lubricant, which may conveniently be a medical grade silicone, to ease tubular passage through the body regions. Endotracheal tube 22 and laryngeal tube 26 are inserted through the mouth of the patient until face shield 46 is adjacent the face of the patient. Stylet bullet guide 75 serves to guide tube 22 into the trachea. Tracheal obturator 30 is inflated by pressurizing through fluid inlet 36. This pressurizing may conveniently be accomplished by the operator simply blowing into fluid inlet 36, thereby opening check valve 40 and introducing air through inflation line 42 into tracheal obturator 30. Pressure indicator balloon 41 on tube 42 indicates the presence of pressure within the obturator and that inflation has been achieved. Pressure relief valve 37 prevents overpressurizing the obturator and prevents damage to the surrounding tissue.

The location of inner end 24 of endotracheal tube 22 is then determined. Stylet bullet guide 75 is removed from tube 22 and respiratory fluid is introduced. If chest movement is observed, the blind intubation has been achieved and resuscitation can be commenced. If no chest movement is observed, the pharyngeal obturator 32 is inflated, if not inflated concurrently with obturator 30. The endotracheal tube 22 may be capped to seal the gastric region and respiratory fluid introduced through inner end 28 of laryngeal tube 26.

The operator now introduces respiratory fluid through the outer end 27 of laryngeal tube 26 or endotracheal tube 22 and, thence, into the patient's lungs. The respiratory fluid may be expired air breathed directly into outer ends 27 or 25 by the operator or may be oxygen and/or air mixture introduced through outer ends 27 or 25 by means of automatically controlled respiratory equipment. According to the present invention, there is no requirement that face shield 46 be sealed against the facial contours of the patient and no operator action is required to maintain any such seal. In the event that automatic respiratory equipment is available, the operator is free to attend to other emergency treatment if needed.

If endotracheal tube 22 enters the esophagus, then respiratory fluid is introduced through laryngeal tube 26 after the obturators have been inflated. This will be apparent when respiratory fluid is applied through endotracheal tube 22 and no chest movement results. If this occurs, the respiratory fluid is being introduced through endotracheal tube 22 directly into the gastric region and the emergency resuscitation is discontinued and the pharyngeal obturator 32 is inflated. Obturator 30 then acts to confine the respiratory fluid to the lungs and prevents the entry of any fluid from the stomach into the lungs. However, the present device should successfully intubate in about 50% of the attempts.

Other advantages of the present emergency resuscitation apparatus will be apparent when the patient has suffered severe injury about the face and throat. It is very difficult to seal around the facial injuries or where the face has been severely burned. Further, the pharyngeal tissues are easily susceptible to injuries and subsequent bleeding in that region can interfere with resuscitation of the victim. The use of a pharyngeal obturator serves to exert pressure against ruptured blood vessels within the pharynx and to stop such bleeding. Further, there is no requirement with the present invention that any sealing be accomplished about the facial contours of the patient.

Yet another advantage of the present invention is obtained where the endotracheal tube has been inserted in the esophagus. The large lumen provided for introducing respiratory fluid into the trachea serves to vent any respiratory fluid which leaks between the tracheal obturator now sealing against the esophagus. Thus, the stomach region remains unpressurized and less subject to aspirating the contents.

Once the position of endotracheal tube 22 is determined, the lower electrode may be positioned in the event defibrillation is needed. Where endotracheal tube 22 has been inserted in the trachea, then either stylet 75 or catheter 50 is inserted through laryngeal tube 26 and into the esopohagus. The appropriate sealing cuff is then inflated to bring the corresponding electrode into contact with the esophageal wall. Where tube 22 has been inserted in the esophagus, tube 22 or stylet 75 must be further inserted for proper electrode placement or stylet 75 may be removed and catheter 50 inserted to the desired location.

The operator preferably verifies contact of the tongue with upper electrodes 58 and/or 33 and connects the various electrodes with defibrillator power supply 70 having a selected power output suitable for use with internal electrodes. Where electrode areas 31 are provided on tracheal cuff 30, electrodes 31 may serve as the upper electrode for use in either the esophagus or the trachea since electrode 31 will generally be located above the heart. Catheter 50 electrode 58 is then positioned below the heart to form the desired current path. The operator may then proceed with emergency resuscitation applying energy as necessary to correct cardiac fibrillation.

It is a feature of the emergency device herein described that a variety of internal locations are available for electrode placement. Referring to FIG. 1, a first path may be formed using electrodes 48 and/or 33 against a tongue area and electrode 58 on the esophageal wall. A second path may be formed using electrode 31 in the trachea and electrode 58 on the esophageal wall.

If the endotracheal tube 22 is inserted in the esophagus, either inadvertently or purposefully, the catheter 50 or stylet 75 (FIG. 3) may be inserted to a position below the heart to obtain both electrodes on the esophageal wall and bracketing the heart. Where an adjustable endotracheal tube 22 is provided, then tube 22 could be inserted an additional amount to place electrode 31 at a location below the heart to form a defibrillating current path in operation with electrodes 33 and/or 48.

It is therefore apparent that the present invention is one well adapted to attain all of the objects and advantages hereinabove set forth, together with other advantages which will become obvious and inherent from a description of the apparatus itself. It will be understood that certain combinations and subcombinations are of utility and may be employed without reference to other features and subcombinations. This is contemplated by and is within the scope of the present invention.

What is claimed is:

1. Emergency medical apparatus, comprising:
a first electrode means adapted for positioning internally of a patient at a location above a heart,
first means for urging said first electrode means into electrical contact with an adjacent body portion of said patient, a second electrode means adapted for positioning within an esophagus at a location below said heart, second means for urging said second electrode means into electrical contact with said esophagus, defibrillating means for energizing said first and second electrode means, and said first and second electrode means being relatively positionable to obtain electrical current from said defibrillating means and within said heart effective to terminate fibrillation of said heart.

2. The apparatus of claim 1, wherein a first electrode means is adjacent a tongue portion of said patient.

3. The apparatus of claim 2, further including:

a laryngeal tube extending through said first urging means and having an outer opening adapted to receive a selected fluid and an inner opening adapted to terminate in a laryngeal region above said second urging means.

4. The apparatus of claim 3, further including:

first means extending through said first urging means for supporting said second electrode means.

5. The apparatus of claim 4, wherein said first support means includes:

an endotracheal tube having an outer opening above said first urging means and an inner opening below said second urging means, said endotracheal tube being selectively positionable at locations including said esophagus at said locations below said heart.

6. The apparatus of claim 5, further including:

a third electrode means adapted for positioning within said esophagus, means for urging said third electrode means into electrical contact with said esophagus, and second means supporting said third urging means and insertable through said laryngeal tube and said endotracheal tube to position said third urging means below said heart.

7. The apparatus of claim 4, wherein said first support means is insertable through said laryngeal tube to position said second electrode means below said heart.

8. The apparatus of claim 4, further including:

a shield member adapted to position and protect said laryngeal tube and said first support means within an oral cavity.

9. The apparatus of claim 8, wherein said shield member includes a portion forming said first urging means.

10. The apparatus of claim 1, 2, 3, 4, 5, 6, 7 or 8, wherein said first urging means is adapted for expanding by at least human breath to a volume effectively filling a pharyngeal region and sealing oral and nasal passages extending therefrom.

11. The apparatus of claim 1, wherein said first electrode means is adjacent a tracheal or esophageal body portion.

12. The apparatus of claim 11, further including first means for supporting said first electrode means and said first urging means.

13. The apparatus of claim 12, wherein said first support means includes:

an endotracheal tube having an outer opening above said first urging means and an inner opening below said first urging means, said endotracheal tube being adapted for selectively positioning within said trachea or said esophagus.

14. The apparatus of claim 13, further including a laryngeal tube in operative relationship with said endotracheal tube and having an inner opening above said first urging means.

15. The apparatus of claim 14, further including:

second means for supporting said second urging means and said second electrode means.

16. The apparatus of claim 15, further including:

a shield member adapted to position and protect said laryngeal tube and endotracheal tube within an oral cavity.

17. The apparatus of claims 14, 15, or 16, further including:

a pharyngeal cuff surrounding said laryngeal tube and said tracheal tube and adapted for expanding by at least human breath to a volume effectively filling a pharyngeal region and sealing oral and nasal passages extending therefrom.

* * * * *